Figure 1:
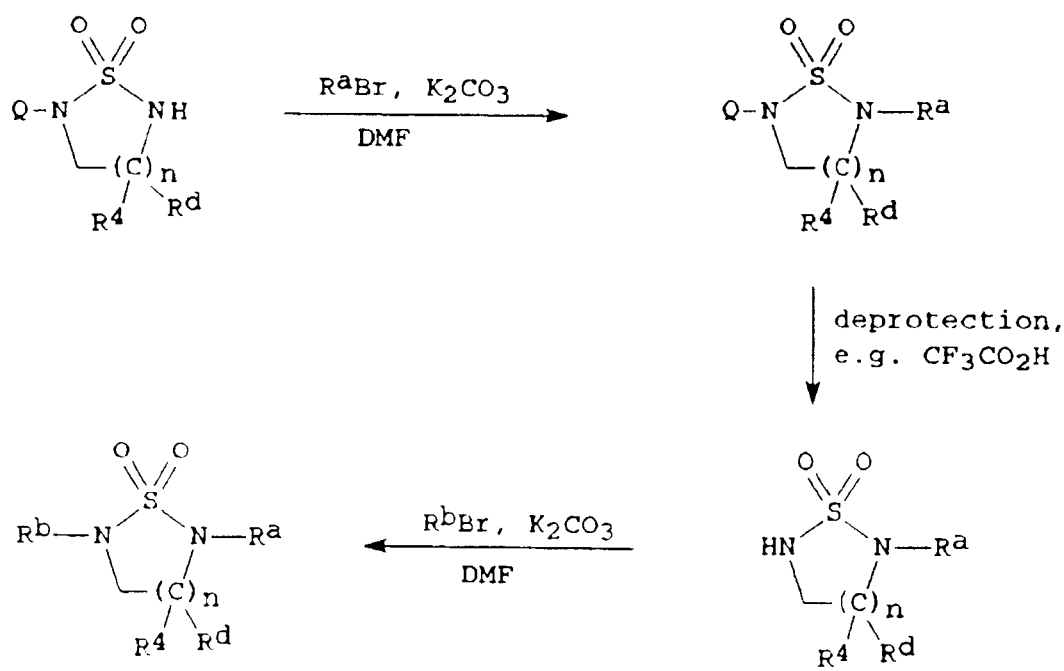

United States Patent [19]
McDonald et al.

[11] Patent Number: 6,159,994
[45] Date of Patent: Dec. 12, 2000

[54] HISTAMINE $H_3$ RECEPTOR LIGANDS

[75] Inventors: Iain Mair McDonald, Paddock Wood; David John Dunstone, Orpington; Matthew John Tozer, London, all of United Kingdom

[73] Assignee: James Black Foundation, London, United Kingdom

[21] Appl. No.: 09/462,910

[22] PCT Filed: Jul. 14, 1998

[86] PCT No.: PCT/GB98/02062

§ 371 Date: Mar. 13, 2000

§ 102(e) Date: Mar. 13, 2000

[87] PCT Pub. No.: WO99/05141

PCT Pub. Date: Feb. 4, 1999

[30] Foreign Application Priority Data

Jul. 25, 1997 [GB] United Kingdom .................... 9715816

[51] Int. Cl.[7] ........................ C07D 417/06; A01K 31/433
[52] U.S. Cl. ............................. 514/362; 548/134
[58] Field of Search ................. 548/134; 514/362

[56] References Cited

U.S. PATENT DOCUMENTS 5,580,889 12/1996 Shiokawa ................................ 514/343

FOREIGN PATENT DOCUMENTS

| | | | |
|---|---|---|---|
| EP 0 458 661 A | 11/1991 | European Pat. Off. . | |
| WO 95 0637 A | 3/1995 | WIPO . | |
| WO 97 17345 A | 4/1997 | WIPO . | |

OTHER PUBLICATIONS

Aran et al., "Reactivity of 4–amino–2–benzyl–2,3–dihydro–3–oxo–1,2,5–thiadiazole 1,1–dioxide towards amines: synthesis of potential histamine H–receptor antagonists," *J. Chem. Soc.*, 1:955–959 (1987).

Hoffman et al., "Conformational requirements for hisamine H–2–receptor inhibitors: A structure–activity of phenylene analogues related to cimetidine and tiotidine," *J. of Med. Chem.* 26:140–144 (1983).

*Primary Examiner*—Robert Gerstl
*Attorney, Agent, or Firm*—Foley & Lardner

[57] ABSTRACT

Compounds of formula (I) and pharmaceutically acceptable salt thereof are useful as histamine $H_3$ receptor ligands. $R^1$ is an optional substituent such as $C_1$ to $C_6$ alkyl. The moiety (1) replaces any available hydrogen atom on a carbon or nitrogen atom in the ring which includes X. $R^2$ is $C_1$ to $C_8$ hydrocarbylene (in which one or more hydrogen atoms may be replaced by halogen atoms, and up to 2 carbon atoms may be replaced by oxygen, nitrogen or sulfur atoms); $R^3$ replaces any available hydrogen atom on a carbon or nitrogen atom in the ring which includes X, and is hydrogen or $C_1$ to $C_{15}$ hydrocarbyl (in which one or more hydrogen atoms may be replaced by halogen atoms, and up to 3 carbon atoms may be replaced by oxygen, nitrogen or sulfur atoms); the (or each) $R^4$ group is independently selected from H, non-aromatic $C_1$ to $C_6$ hydrocarbyl, and aryl ($C_1$ to $C_3$ alkyl); X is —SO— or —$SO_2$—; Y and Z are each hydrogen, or together represent =O or —N—$R^5$, wherein $R^5$ is H, non-aromatic $C_1$ to $C_6$ hydrocarbyl, or aryl ($C_1$ to $C_3$ alkyl), or one of Y and Z is non-aromatic $C_1$ to $C_6$ hydrocarbyl, or aryl ($C_1$ to $C_3$ alkyl) and the other is H; a is from 0 to 2; and n is 1 or 2.

12 Claims, 7 Drawing Sheets

HISTAMINE H₃ RECEPTOR LIGANDS

This invention relates to compounds which bind to histamine H₃ receptors, and to methods of making such compounds.

Histamine is well known as a mediator in certain hypersensitive reactions of the body, such as allergic rashes, hayfever and asthma. These conditions are now commonly treated with potent antagonists of histamine, so-called "antihistamines".

In the 1940s, it was noted that some physiological effects of histamine, such as increased gastric acid secretion and cardiac stimulation, were not blocked by the antihistamines which were then available. This led to the proposal that histamine receptors exist in at least two distinct types, referred to as H₁ and, H₂ receptors. Subsequently, H₂ antagonists (such as cimetidine, ranitidine and famotidine) were identified, and they have become important in the treatment of gastric ulcers.

In the early 1980s, it was established that histamine also has a role as a neurotransmitter in the central nervous system. Arrang et al., Nature 302, 832 to 837 (1983), proposed the existence of a third histamine receptor subtype (H₃) located presynaptically on histaminergic nerve endings. Arrang et al. postulated that the H₃ receptor is involved in inhibiting the synthesis and release of histamine in a negative feedback mechanism. The existence of the H₃ receptor was subsequently confined by the development of selective H₃ agonists and antagonists (Arrang et al., Nature 327, 117 to 123 (1987)). The H₃ receptor has subsequently been shown to regulate the release of other neurotransmitters both in the central nervous system and in peripheral organs, in particular in the lungs and GI tract. In addition, H₃ receptors are reported to regulate the release of histamine from mast cells and enterochromaffin-like cells.

A need exists for potent and selective H₃ ligands (both agonists and antagonists) as tools in the study of the role of histamine as a neurotransmitter, and in its roles as a neuro-, endo- and paracrine hormone. It has also been anticipated that H₃ ligands will have therapeutic utility for a number of indications including use as sedatives, sleep regulators, anticonvulsants, regulators of hypothalamo-hypophyseal secretion, antidepressants and modulators of cerebral circulation, and in the treatment of asthma and irritable bowel syndrome.

A number of imidazole derivatives have been proposed in the patent literature as H₃ ligands. Representative are the disclosures of EP-A-0197840, EP-A-0214058, EP-A-0458661, EP-A-0494010, EP-A-0531219, WO91/17146, WO92/15567, WO93/01812, WO93/12093, WO93/12107, WO93/12108, WO93/14070, WO93/20061, WO94/17058, WO95/06037, WO95/11894, WO95/14007, U.S. Pat. No. 4,988,689 and U.S. Pat. No. 5,217,986.

According to the present invention, there is provided a compound of the formula

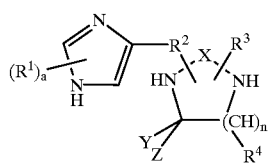

(I)

wherein $R^1$ is selected from $C_1$ to $C_6$ alkyl, $C_1$ to $C_6$ alkoxy, $C_1$ to $C_6$ alkylthio, carboxy, carboxy ($C_1$ to $C_6$) alkyl, formyl, $C_1$ to $C_6$ alkylcarbonyl, $C_1$ to $C_6$ alkylcarbonylalkoxy, nitro, trihalomethyl, hydroxy, amino, $C_1$ to $C_6$ alkylamino, di($C_1$ to $C_6$ alkyl) amino, aryl, $C_1$ to $C_6$ alkylaryl, halo, sulfamoyl and cyano;

the moiety

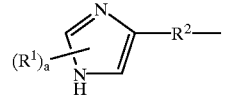

replaces any available hydrogen atom on a carbon or nitrogen atom in the ring which includes X;

$R^2$ is $C_1$ to $C_8$ hydrocarbylene in which one or more hydrogen atoms may be replaced by halogen atoms, and up to 2 carbon atoms may be replaced by oxygen, nitrogen or sulfur atoms, provided that $R^2$ does not contain a —O—O— group;

$R^3$ replaces any available hydrogen atom on a carbon or nitrogen atom in the ring which includes X, and is hydrogen or $C_1$ to $C_{15}$ hydrocarbyl, in which one or more hydrogen atoms may be replaced by halogen atoms, and up to 3 carbon atoms may be replaced by oxygen, nitrogen or sulfur atoms, provided that $R^3$ does not contain a —O—O— group;

the (or each) $R^4$ group is independently selected from H, non-aromatic $C_1$ to $C_6$ hydrocarbyl, and aryl ($C_1$ to $C_3$ alkyl);

X is —SO— or —SO₂—

Y and Z are each hydrogen, or together represent =O or =N—$R^5$, wherein $R^5$ is H, non-aromatic $C_1$ to $C_6$ hydrocarbyl, or aryl ($C_1$ to $C_3$ alkyl), or one of Y and Z is non-aromatic $C_1$ to $C_6$ hydrocarbyl, or aryl ($C_1$ to $C_3$ alkyl), and the other is H;

a is from 0 to 2 (preferably 0); and n is 1 or 2 and pharmaceutically acceptable salts thereof.

Preferably, $R^2$ is $C_1$ to $C_6$ hydrocarbylene.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", Drug Delivery Systems, pp. 112–176 (1985), and Drugs, 29, pp.455–473 (1985).

Pro-drug forms of the pharmacologically-active compounds of the invention will generally be compounds according to formula (I) having an acid group which is esterified or amidated. Included in such esterified acid groups are groups of the form —COOR⁶, wherein $R^6$ is $C_1$ to $C_5$ alkyl, phenyl, substituted phenyl, benzyl, substituted benzyl, or one of the following:

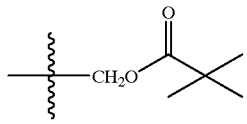

-continued
or

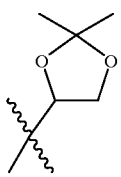

Amidated acid groups include groups of the formula —CONR$^7$R$^8$, wherein R$^7$ is H, C$_1$ to C$_5$ allyl, phenyl, substituted phenyl, benzyl, or substituted benzyl, and R$^8$ is —OH or one of the groups just recited for R$^7$.

Compounds of formula (I) having an amino group may be derivatised with a ketone or an aldehyde such as formaldehyde to form a Mannich base. This will hydrolyse with first order kinetics in aqueous solution.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

The compounds of the invention may exist in various enantiomeric, diastereomeric and tautomeric forms. It will be understood that the invention comprehends the different enantiomers, diastereomers and tautomers in isolation from each other, as well as mixtures of enantiomers, diastereomers and tautomers.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups. The term "hydrocarbylene" refers to corresponding divalent groups, the two free valencies being on separate atoms.

When reference is made herein to a carbon atom of a hydrocarbyl group being replaced by O, S or N, it will be understood that what is meant is that a —CH$_2$— group is replaced by —O— or —S—, or that

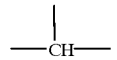

is replaced by

A "carbocyclic" group, as the term is used herein, comprises one or more closed chains or rings, which consist entirely of carbon atoms, and which may be substituted. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above, which may be substituted.

When reference is made herein to a substituted carbocyclic group (such as substituted phenyl), the substituents are preferably from 1 to 3 in number and selected from C$_1$ to C$_6$ alkyl, C$_1$ to C$_6$ alkoxy, C$_1$ to C$_6$ alkylthio, carboxy, carboxy (C$_1$ to C$_6$)alkyl, formyl, C$_1$ to C$_6$ alkylcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl) amino, aryl, C$_1$ to C$_6$ alkylaryl, halo, sulfamoyl and cyano.

The term "halogen", as used herein, refers to any of fluorine, chlorine, bromine and iodine.

We have found that a number of compounds in the prior art have shown a significant discrepancy in their activity as measured by two ileum based assays which are described below. We would interpret discrepancies between the functional and binding assays of greater than about 0.5 log units as significant. Analysis of data obtained in these particular functional and radioligand binding assays and also in other related bioassays suggests that the discrepancy may be connected, at least in part, with residual efficacy inherent in these structures. In practice, this means that these particular compounds may act as agonists, at least in some tissues.

Surprisingly, we have found that the majority of compounds disclosed herein do not show a significant discrepancy in the two assays. Thus, these compounds may be considered to have minimal potential to express agonist action, and would be expected to behave as antagonists or, at constitutively-active receptors, as inverse agonists. In one aspect, therefore, the present invention provides the use of these compounds as histamine antagonists or inverse agonists, and in the manufacture of medicaments for this purpose.

Pharmaceutically acceptable salts of the acidic or basic compounds of the invention can of course be made by conventional procedures, such as by reacting the free base or acid with at least a stoichiometric amount of the desired salt-forming acid or base.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is miixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 μg/kg and 50 mg/kg, especially between 10 μg/kg and 10 mg/kg, eg. between 100 μg/kg and 2 mg/kg.

The Figures illustrate a number of methods for preparing the compounds of the invention, which are depicted in the form

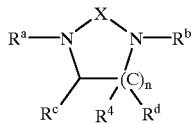

In this structure, one of $R^a$, $R^b$, $R^c$ and $R^d$ corresponds to $R^3$, another corresponds to the moiety

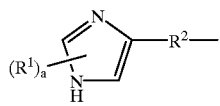

and two (or three if n=2) are H.

FIG. 1 illustrates a general synthetic route for compounds according to the invention which are of the form

Figure 2:
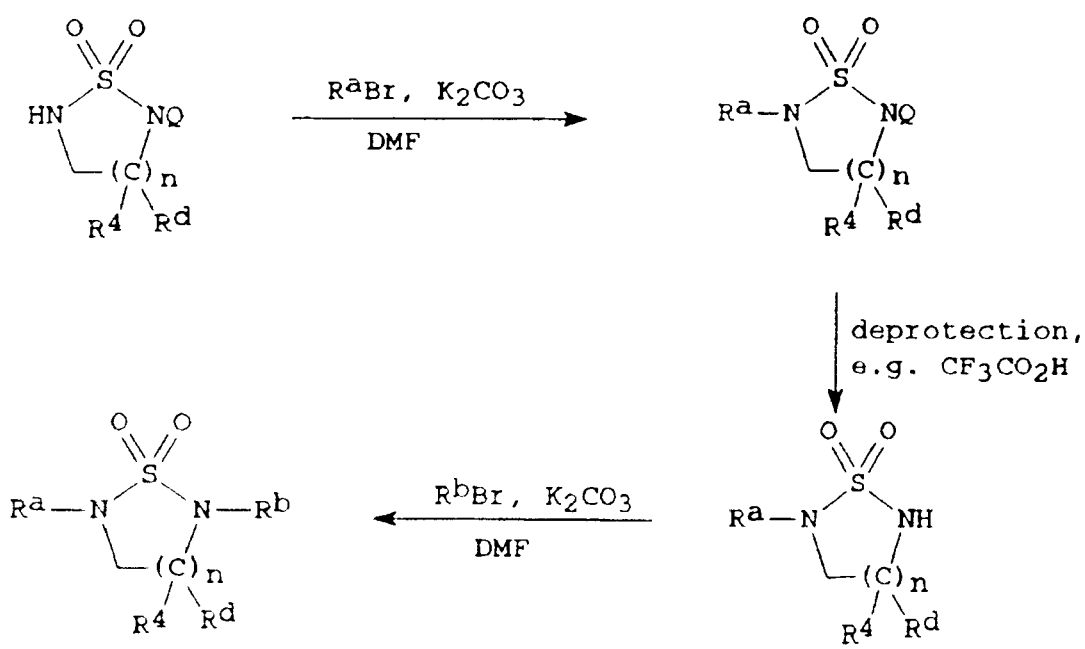

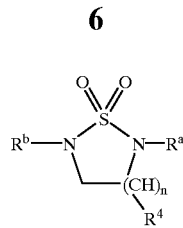

ie. compounds of Formula I in which X is —SO$_2$—, and Y and Z are H. In FIG. 1, Q represents a protecting group, such as t-butyl. FIG. 1 shows the use of $R^aBr$ to introduce the moiety $R^a$ as a substituent on the thiadiazolidine ring, but it will be understood that other alkylating agents can be used instead. It will also be understood that the order in which the moieties $R^a$ and $R^b$ are introduced as substituents on the thiadiazolidine ring is not critical. The reverse order is illustrated in FIG. 2.

Figure 3:
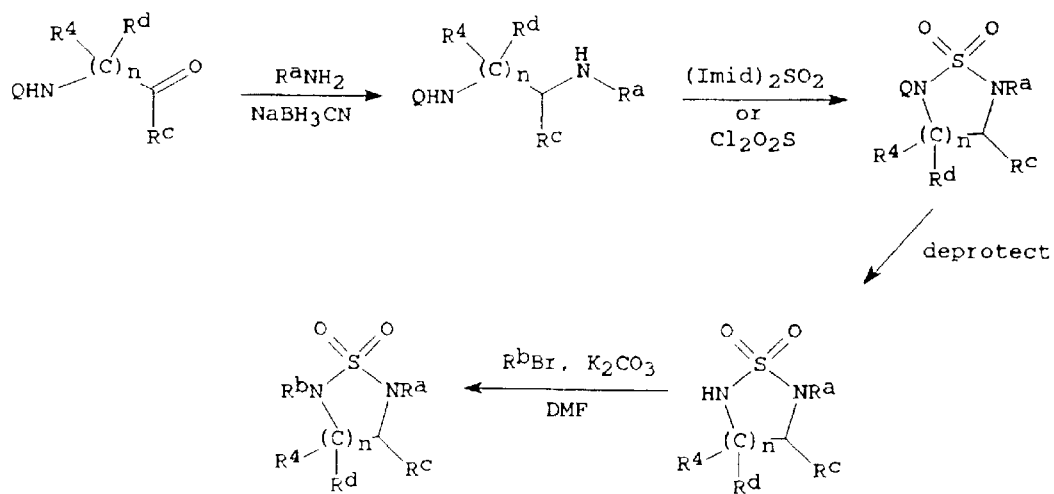

FIG. 3 illustrates one method for preparing compounds according to the invention which are of the form

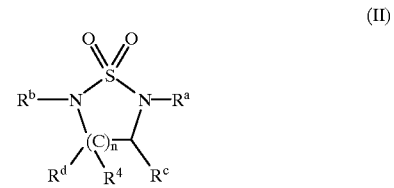

ie. compounds of Formula I in which X is —SO$_2$—, Y is H and Z is $R^c$.

Figure 4:
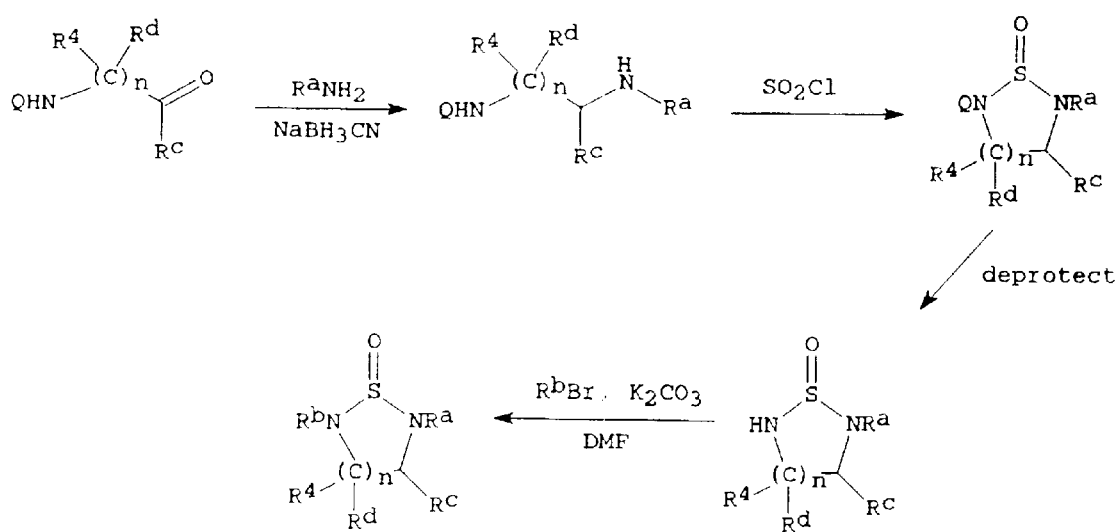

FIG. 4 illustrates an analogous method for preparing compounds of the form

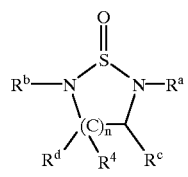

Figure 5:
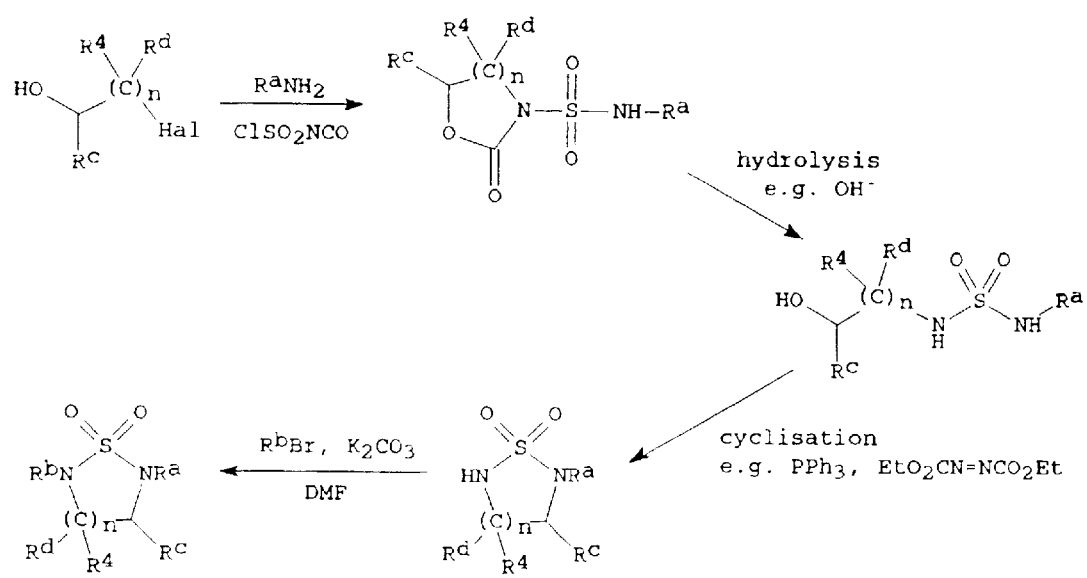

A further method for preparing compounds of formula II is shown in FIG. 5.

Compounds of the form

Figure 6:
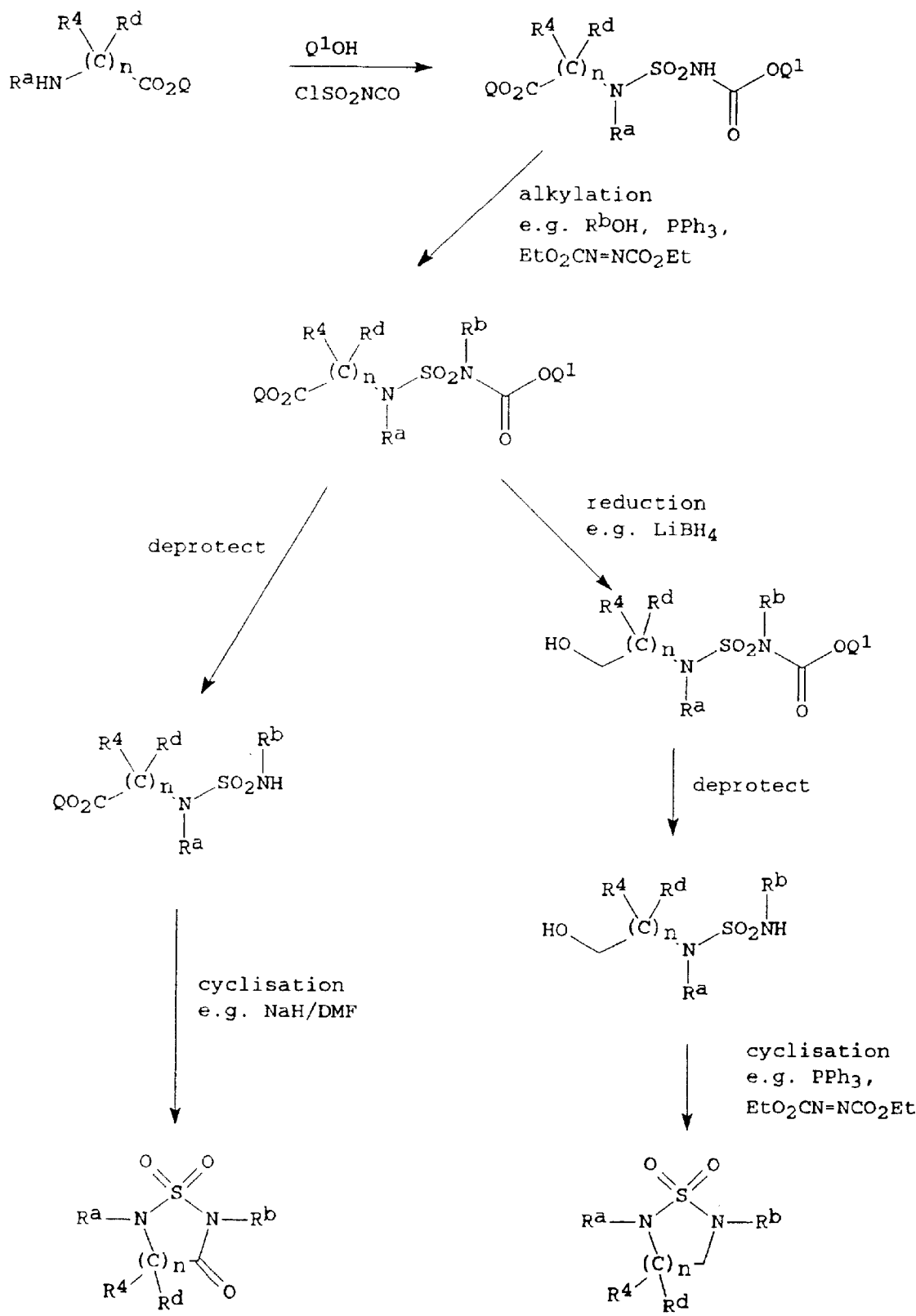

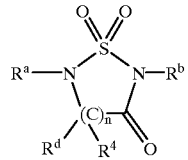

can conveniently be prepared by the method which is illustrated in FIG. 6. Q represents a group such as methyl or benzyl, and $Q^1$ represents a group such as t-butyl or benzyl.

FIG. 6 also illustrates an alternative synthetic route to compounds of the form

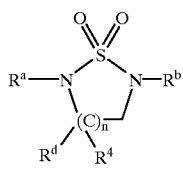

while compounds of the form

Figure 7:
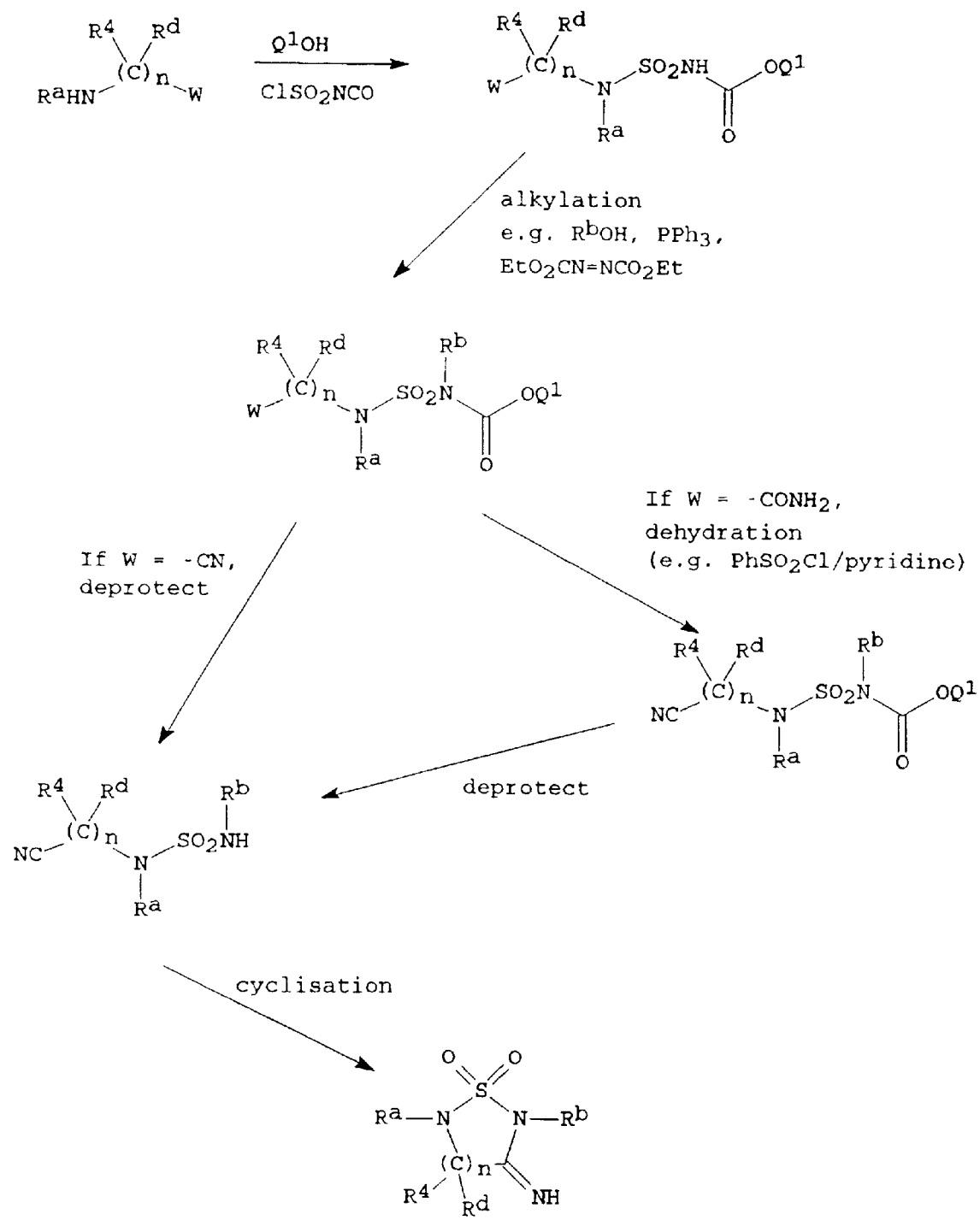

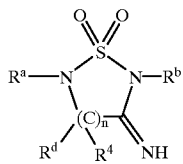

may be prepared by either of the methods shown in FIG. 7. The initial part of these syntheses is similar to that shown in FIG. 6, except that W represents —$CONH_2$ or —CN. If $R^5$ is other than H, this group may be introduced into the molecule by well-known methods.

The invention is now further illustrated by means of the following examples.

Example 1

4-(4-chlorophenyl)methyl-2-(5-(4-imidazolyl)pentyl)-1,2,5-thiadiazolidine-1,1-dioxide

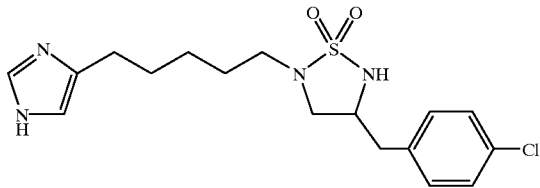

step 1. N-tert-butyloxycarbonyl N'-(1-carboxymethyl-2-(4-chlorophenyl))ethyl sulfamide 2-Methyl-2-propanol (7.75 ml, 81 mmol) was added dropwise over 5 minutes to a solution of chlorosulfonyl isocyanate (4.5 ml, 51.7 mmol) in dry dichloromethane (40 ml) under argon at 0° C. The solution was allowed to warm to room temperature and after stirring for 45 minutes was added dropwise over 20 minutes to a solution of (d/l)4-chlorophenylalanine methyl ester hydrochloride (10 g, 40 mmol) and triethylamine (11.3 ml, 81 mmol) in dry dichloromethane (60 ml) under argon at 0° C. The reaction mixture was allowed to warm to room temperature and stirred for 3 hours. The solution was washed successively with 5% $KHSO_4$ solution (150 ml), saturated $NaHCO_3$ solution (150 ml), brine (2×100 ml) and dried ($MgSO_4$). Filtration and evaporation of the solvent gave the crude product which was triturated with ether-hexane to afford a pale solid. (13.4 g; 85%)

step 2. N-tert-butyloxycarbonyl N-5-(4-($N^{im}$-triphenylmethyl)imidazolyl)pentyl N'-(1-carboxymethyl-2-(4-chlorophenyl))ethyl sulfamide Diethylazodicarboxylate (1.29 ml, 8.2 mmol) was added to a solution of 5-(4-($N^{im}$-triphenylmethyl)imidazolyl) pentanol (3.23 g, 8.1 mmol), N-tert-butyloxycarbonyl N'-1-carboxymethyl-2-(4-chlorophenyl)ethyl sulfamide (3.20 g, 8.1 mmol), and triphenylphosphine (2.14 g, 8.2 mmol) in dry THF (60 ml) under argon at 0° C. The reaction mixture was allowed to warm to room temperature and stirring continued for 17 hours. The solvent was evaporated and the crude product purified by flash chromatography on silica gel with ethyl acetate-dichloromethane (1:10) as eluant to give the product as an white fluffy solid. (4.42 g; 70%)

step 3. N-tert-butyloxycarbonyl N-5-(4-($N^{im}$-triphenylmethyl)imidazolyl)pentyl N'-1-(4-chlorophenyl)methyl-2-hydroxyethyl sulfamide Sodium borohydride (2.05 g, 54 mmol) and lithium chloride (2.26 g, 53 mmol) were added in portions to a solution of N-tert-butyloxycarbonyl N-5-(4-($N^{im}$-triphenylmethyl)imidazolyl)pentyl-N'-1-carboxymethyl-2-(4-chlorophenyl)ethyl sulfamide (3.42 g, 4.43 mmol) in methanol-THF (3:2/150 ml) at room temperature. After stirring at room temperature for 36 hours the reaction mixture was evaporated to dryness and the residue partitioned between water-dichloromethane (1:1/160 ml). The organic layer was separated, washed with brine (70 ml) and dried ($MgSO_4$). Filtration and evaporation of the solvent gave the crude product which was purified by flash chromatography on silica gel with methanol-dichloromethane (1:20) as eluant. The product was obtained as a pale solid (3.0 g; 92%).

step 4. N-5-(4-($N^{im}$-triphenylmethyl)imidazolyl)pentyl N'-1-(4chlorophenyl)methyl-2-hydroxyethyl sulfamide 4N HCl in dioxan (19 ml) was added to a solution of N-tert-butyloxycarbonyl N-5-(4-($N^{im}$-triphenylmethyl)imidazolyl)pentyl N'-1-(4-chlorophenyl)methyl-2-hydroxyethyl sulfamide (3.0 g, 4.0 mmol) in dioxan (60 ml) at room temperature under argon. After stirring at room temperature for 17 hours the mixture was evaporated to dryness and the residue partitioned between ethyl acetate-saturated $NaHCO_3$ solution (1:1/80 ml). The organic layer was separated and dried ($MgSO_4$). Filtration and evaporation of the solvent gave the product as a white solid (1.93 g; 74%).

step 5. 4-(4chlorophenyl)methyl-2-(5-(4-($N^{im}$-triphenylmethyl)imidazolyl)pentyl)-1,2,5-thiadiazolidine-1,1-dioxide Diethylazodicarboxylate (0.48 ml, 3.0 mmol) was added to a solution of N-5-(4-($N^{im}$-triphenylmethyl)imidazolyl) pentyl N'-1-(4-chlorophenyl)methyl-2-hydroxyethyl sulfamide (1.93 g, 3.0 mmol), and triphenylphosphine (0.79 g, 3.0 mmol) in dry THF (40 ml) under argon at 0° C. The reaction mixture was allowed to warm to room temperature and after stirring for 17 hours was evaporated to dryness. The crude product was purified by flash chromatography on silica gel with methanol-dichloromethane (1:20) as eluant to give the product as an oil (1.78 g; 95%).

step 6. 4-(4chlorophenyl)methyl-2-(5-(4-imidazolyl)pentyl)-1,2,5-thiadiazolidine-1,1-dioxide A solution of 4-(4-chlorophenyl)methyl-2-(5-(4-($N^{im}$-triphenylmethyl)imidazolyl)pentyl)-1,2,5-thiadiazolidine-1,1-dioxide (1.78 g, 2.9 mmol) in trifluoracetic acid (15 ml) was stirred at room temperature for 18 hours. The reaction mixture was evaporated to dryness and the residue dissolved in ethyl acetate (50 ml), washed with saturated $NaHCO_3$ solution (40 ml), brine (40 ml) and dried ($MgSO_4$). Filtration and evaporation of the solvent gave the crude product as an oil, which was purified by flash chromatography on silica gel with methanol-dichloromethane (1:50 to 3:20) as eluant. The product was obtained as an oil (0.2 g; 18%).

$\delta_H$($CD_3OD$) 1.18–1.74 (6H, m), 2.22–3.92 (9H, m), 6.76 (1H, s), 7.25(4H, m), 7.58(1H, s).

Example 2

(2-(4-imidazolyl)ethyl)-1,2,5-thiadiazolidine-1,1-dioxide

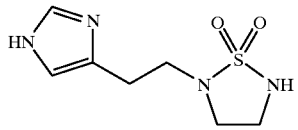

step 1. N-(2-(4-($N^{im}$-triphenylmethyl)imidazolyl)ethyl) sufamoyl-2-oxazolidinone The compound was prepared by a similar method to that used in the preparation of N-tert-butyloxycarbonyl N'-(1-carboxymethyl-2-(4-chlorophenyl))ethyl sulfamide (example 1; step 1) except that 2-bromoethanol and 2-(4-($N^{im}$-triphenylmethyi)imidazolyl)ethylamine were used in place of 2-methyl-2-propanol and (d/l)4-chlorophenylalanine methyl ester hydrochloride respectively.

step 2. N-2-(4-($N^{im}$-triphenylmethyl)imidazolyl)ethyl N'-2-hydroxyethyl sulfamide A solution of N-(2-(4-($N^{im}$-triphenylmethyl)imidazolyl)ethyl)sufamoyl-2-oxazolidinone (6.0 g, 12 mmol) in ethanol (20 ml) was heated at reflux with 2N NaOH solution (15 ml) for 2 minutes. On cooling to room temperature the solution was concentrated in vacuo, and diluted with water. The resultant precipitated solid was isolated by filtration and dried. (0.85 g; 15%)

step 3, 2-(2-(4-imidazolyl)ethyl)-1,2,5-thiadiazolidine-1,1-dioxide

The compound was prepared by a similar method to that used in the preparation of 4-(4-chlorophenyl)methyl-2-(5-(4-imidazolyl)pentyl)-1,2,5-thiadiazolidine-1,1-dioxide (example 1) except that N-2-(4-($N^{im}$-triphenylmethyl) imidazolyl)ethyl N'-2-hydroxyethyl sulfamide was used in place of N-5-(4-($N^{im}$-triphenylmethyl)imidazolyl)pentyl N'-1-(4-chlorophenyl)methyl-2-hydroxyethyl sulfamide in step 5 to obtain 2-(2-(4-($N^{im}$-triphenylmethyl)imidazolyl) ethyl-1,2,5-thiadiazolidine-1,1-dioxide, which was used in place of 4-(4-chlorophenyl)methyl-2-(5-(4-($N^{im}$-triphenylmethyl)imidazolyl)pentyl)-1,2,5-thiadiazolidine-1,1-dioxide in step 6.

$\delta_H$ ($d^6$-DMSO) 2.78(2H, m), 2.96(2H, m), 3.19(4H, s), 7.47(1H, s), 8.97(1H, s)

Example 3

2-(3-(4-imidazolyl)propyl)-1,2,5-thiadiazolidine-1,1-dioxide

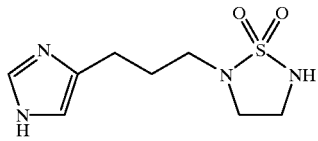

step 1. 5-tert-butyl-2-(3-(4-($N^{im}$-dimethylsufamoyl) imidazolyl)propyl)-1,2,5-thiadiazolidine-1,1-dioxide A mixture of 2-tert-butyl-1,2,5-thiadiazolidine-1,1-dioxide (1.34 g, 7.52 mmol), 4-(3-chloropropyl)-2-tert-butyl-dimethylsilyl-3-dimethylsufamoyl imidazole (2.75 g, 7.5 mmol) and $K_2CO_3$ (1.04 g, 7.5 mmol) in dimethylformamide (15 ml) was heated at 100° C. for 19 hours. The reaction mixture was partitioned between ethyl acetate-water (1:1/100 ml), the organic layer was separated, washed with brine (2×50 ml) and dried ($MgSO_4$). Filtration and evaporation of the solvent gave the crude product which was purified by flash chromatography on silica gel with ethyl acetate as eluant. The product was obtained as a yellow solid (1.6 g; 54%).

step 2. 2-(3-(4-imidazolyl)propyl)-1,2,5-thiadiazolidine-1,1-dioxide

A solution of 5-tert-butyl-2-(3-(4-($N^{im}$-dimethylsufamoyl)imidazolyl)propyl)-1,2,5-thiadiazolidine-1,1-dioxide (0.8, g, 1.6 mmol) in 2N HCl (40 ml) was heated at reflux for 4 hours. The mixture was diluted with water (50 ml), washed with ether (40 ml), and the aqueous solution freeze dried to give the product as a clear gum. (0.43 g; 100%)

$\delta_H$ ($d^6$-DMSO) 2.0(2H, m), 2.78(2H, m), 2.96(2H, m), 3.19(4H, s), 7.47(1H, s), 8.97(1H, s)

Example 4

2-(3-4-imidazolyl)propyl)-1,2,5-thiadiazolidin-3-one-1,1-dioxide

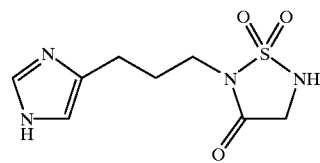

step 1. N-tert-butyloxycarbonyl N-3-(4-($N^{im}$-triphenyhmethyl)imidazolyl)propyl N'-benzyloxycarbonylmethyl sulfamide The compound was prepared by a similar method to that used in the preparation of N-tert-butyloxycarbonyl N-5-(4-($N^{im}$-triphenylmethyl)imidazolyl)pentyl N'-(1-carboxymethyl-2-(4-chlorophenyl))ethyl sulfamide (example 1, step 2) except that glycine benzyl ester p-toluenesulfonate was used in place of (d/l)4-chlorophenylalanine methyl ester hydrochloride in step 1 to obtain N-tert-butyloxycarbonyl N'-benzyloxycarbonylmethyl sulfamide. N-tert-butyloxycarbonyl N'-benzyloxycarbonylmethyl sulfamide and 3-(4-($N^{im}$-triphenylmethyl)imidazolyl)propanol were used in step 2 in place of N-tert-butyloxycarbonyl N'-1-carboxymethyl-2-(4-chlorophenyl)ethyl sulfamide and 5-(4-($N^{im}$-triphenylmethyl)imidazolyl)pentanol respectively.

step 2. N-3-(4-($N^{im}$-triphenylmethyl)imidazolyl)propyl N'-benzyloxycarbonylmethyl sulfamide The compound was prepared by a similar method to that used in the preparation of N-5-(4-($N^{im}$-triphenylmethyl) imidazolyl)pentyl N'-1-(4-chlorophenyl)methyl-2-hydroxyethyl sulfamide (example 1, step 4) except that N-tert-butyloxycarbonyl N-3-(4($N^{im}$-triphenylmethyl) imidazolyl)propyl N'-benzyloxycarbonylmethyl sulfamide was used in place of N-5-(4-($N^{im}$-triphenylmethyl) imidazolyl)pentyl N'-1-(4-chlorophenyl)methyl-2-hydroxyethyl sulfamide.

step 3. 2-(3-(4($N^{im}$-triphenylmethyl)imidazolyl)propyl)-1,2,5-thiadiazolidin-3-one-1,1-dioxide A solution of N-3-(4-($N^{im}$-triphenylmethyl)imidazolyl) propyl N'-benzyloxycarbonylmethyl sulfamide (3.97 g, 6.7 mmol) in dry DMF (20 ml) was added dropwise over 15 minutes to a suspension of sodium hydride (60% in mineral oil/0.33 g, 8.8 mmol) in DMF (10 ml) at room temperature under argon. After stirring at room temperature for 5 hours the reaction mixture was partitioned between dichloromethane-saturated NaHCO$_3$ solution (1:1/200 ml). The organic layer was separated, washed with brine (50 ml) and dried (MgSO$_4$). Filtration and evaporation of the solvent gave the product as a yellow oil (0.6 g, 19%).

step 4. 2-(3-(4-imidazolyl)propyl)1,2,5-thiadiazolidin-3-one-1,1-dioxide

The compound was prepared by a similar method to that used in the preparation of 4-(4-chlorophenyl)methyl-2-(5-(4-imidazolyl)pentyl)-1,2,5-thiadiazolidine-1,1-dioxide (example 1, step 6) except that 2-(3-(4-(N$^{im}$-triphenylmethyl)imidazolyl)propyl)-1,2,5-thiadiazolidin-3-one-1,1-dioxide was used in place of 4(4-chlorophenyl)methyl-2-(5-(4-(N$^{im}$-triphenylmethyl)imidazolyl)pentyl)-1,2,5-thiadiazolidine-1,1-dioxide.

$\delta_H$ (CDCl$_3$) 1.96(2H, m), 2.70(2H, t), 3.54(2H, t), 4.08 (2H, s), 7.41(1H, s), 8.60(1H, bs), 8.96(1H, d).

Example 5

5-benzyl-2-(3-(4-imidazolyl)propyl)-1,2,5-thiadiazolidine-1,1-dioxide

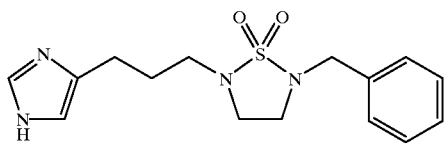

step 1. 2-(3-(4(N$^{im}$-dimethylsufamoyl)imidazolyl)propyl)-1,2,5-thiadiazolidine-1,1-dioxide The compound was prepared by a similar method to that used in the prepartaion of 4-(4-chlorophenyl)methyl-2-(5-(4-imidazolyl)pentyl)- 1,2,5-thiadiazolidine-1,1-dioxide (example 1, step 6) except that 5-tert-butyl-2-(3-(4-(N$^{im}$-dimethylsufamoyl)imidazolyl)propyl)-1,2,5-thiadiazolidine-1,1-dioxide (example 3, step 1) was used in place of 4-(4-chlorophenyl)methyl-2-(5-(4-(N$^{im}$-triphenylmethyl)imidazolyl)pentyl)-1,2,5-thiadiazolidine-1,1-dioxide.

step 2. 5-benzyl-2-(3-(4-imidazolyl)propyl)-1,2,5-thiadiazolidine- 1,1-dioxide

A mixture of 2-(3-(4-(N$^{im}$-dimethylsufamoyl)imidazolyl)propyl)-1,2,5-thiadiazolidine-1,1-dioxide (0.6 g, 1.8 mmol), benzyl bromide (0.2 ml, 1.8 mmol), and K$_2$CO$_3$ (0.23 g, 1.8 mmol) was heated in DMF (10 ml) at 100° C. for 24 hours. The reaction mixture was diluted with water (40 ml), and extracted with dichloromethane (2×40 ml). The extracts were washed with brine (50 ml) and dried (MgSO$_4$). Filtration and evaporation of the solvent gave the crude product as a red oil which was purified by flash chromatography on silica gel with ammonia-methanol-dichloromethane (1:10:90) as eluant. The product was obtained as a yellow oil (0.1 g; 17%).

$\delta_H$(d$^6$-DMSO) 1.78(2H, m), 2.46(2H, t), 2.85(2H, t), 3.24(2H, m), 5.11(2H, s), 7.08(1H, bs), 7.30(5H, m), 6.87 (1H, s), 7.61(1H, s).

Example 6

2-(4-imidazolyl)ethyl-4(S)-methyl-1,2,5-thiadiazolidine-1-oxide

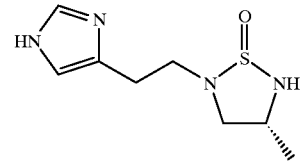

step 1. N-tert-butyloxycarbonyl-4-aza-2(S)-methyl-6-(4-(N$^{im}$-triphenylmethyl)imidazolyl)hexylamine Sodium cyanoborohydride (0.5 g, 7.8 mmol) was added to a solution of 2(S)-tert-butyloxycarbonylaminopropionaldehyde (1.34 g, 7.7 mmol), and 2-(4-(N$^{im}$-triphenylmethyl)imidazolyl) ethylamine (2.73 g, 7.7 mmol) in methanol (80 ml) and 3A$^0$ molecular sieves (1.5 g) at room temperature. After stirring for 17 hours the mixture was filtered and evaporated to dryness. The residue was dissolved in dichloromethane (40 ml) washed with brine (50 ml) and dried (MgSO$_4$). Filtration and evaporation of the solvent gave the crude product as a fluffy solid, which was purified by flash chromatography on silica gel with methanol-dichloromethane (1:25) as eluant. The product was obtained as a white solid. (1.2 g;31%).

step 2. 5-tert-butyloxycarbonyl-4(S)-methyl-2-(4-(N$^{im}$-triphenylmethyl)imidazolyl)ethyl-1,2,5-thiadiazolidine-1-oxide Thionyl chloride (0.3 ml, 4.0 mmol) was added over 5 minutes to a solution of N-tert-butyloxycarbonyl-4-aza-2 (S)-methyl-6-(4-(N$^{im}$-triphenylmethyl)imidazolyl) hexylamine (1.0 g, 2.0 mmol) and triethylamine (1.4 ml, 10 mmol) in dry dichloromethane (100 ml) under argon at −78° C. The reaction mixture was allowed to warm to room temperature and stirring continued for 17 hours. The solution was washed with 10% citric acid solution (60 ml), saturated NaHCO$_3$ solution (60 ml), brine (60 ml) and dried (MgSO$_4$). Filtration and evaporation of the solvent gave the crude product which was purified by flash chromatography on silica gel with methanol-dichloromethane (1:20 to 1:10) as eluant. The product was obtained as a yellow solid (0.63 g; 58%)

step 3. 4-(S)-methyl-3-(4-imidazolyl)propyl-1,2,5-thiadiazolidine-1-oxide

The compound was prepared by a similar method to that used in the preparation of 4(4-chlorophenyl)methyl-2-(5-(4-imidazolyl)pentyl)-1,2,5-thiadiazolidine-1,1-dioxide (example 1, step 6) except that 5-tert-butyloxycarbonyl-4 (S)-methyl-2-(4-(N$^{im}$-triphenylmethyl)imidazolyl)ethyl-1,2, 5-thiadiazolidine-1-oxide was used in place of 4-(4-chlorophenyl)methyl-2-(5-(4-(N$^{im}$-triphenylmethyl) imidazolyl)pentyl)-1,2,5-thiadiazolidine-1,1-dioxide.

$\delta_H$(d$^6$-DMSO) 1.31(3H, m), 3.0–3.7(7H, m), 7.56(1H, s), 9.06(1H, s).

Example 7

2-(4-(4-imidazolyl)butyl)-4-(4-chlorophenyl)methyl-1,2,5-thiadiazolidin-3-one-1,1-dioxide

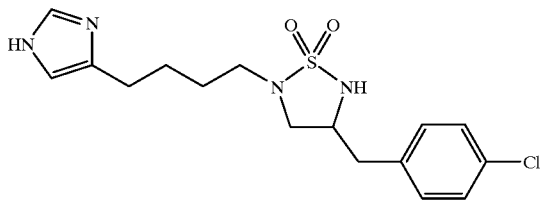

The compound was prepared by a similar method to that used in the preparation of 2-(3-(4-imidazolyl)propyl)-1,2,5-thiadiazolidin-3-one-1,1-dioxide (example 4), except that (d/l)-4-chlorophenylalanine methyl ester hydrochloride and 4-(4-($^{im}$N-triphenylmethyl)imidazolyl)butanol were used in step 1 in place of glycine benzyl ester p-toluenesulfonate and 3-(4-($^{im}$N-triphenylmethyl)imidazolyl)propanol respectively.

$\delta_H$ (d$^6$-DMSO) 1.59(4H, s), 2.64(2H, s), 2.87 and 3.10 (2H, dd×2), 3.50(2H, s), 4.58(1H,m), 7.20–7.43(5H, m), 8.60(1H, bs), 8.97(1H,s), 14.17(1H, bs).

Example 8

2-(4-(4-imidazolyl)butyl)-1,2,5-thiadiazolidin-3-one-1,1-dioxide

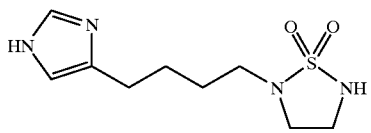

The compound was prepared by a similar method to that used in the preparation of 2-(3-(4-imidazolyl)propyl)-1,2,5-thiadiazolidin-3-one-1,1-dioxide (example 4) except that 4-(4-($^{im}$N-triphenylmethyl)imidazolyl)butanol was used in step 1 in place of 3-(4-($^{im}$N-triphenylmethyl)imidazolyl)propanol.

$\delta_H$(d$^6$-acetone) 1.64–1.77(4H,m), 2.63(2H,t), 3.58(2H,t), 4.09(2H,s), 6.84(1H, s), 7.31(2H, bs), 7.65(1H, s).

The biological activity of the compounds of the examples was measured using the ileal longitudinal muscle, myenteric plexus assay described by Paton and Aboo Zar (J. Physiol. 1968, 194, 13–33). Male Dunkin-Hartley guinea pigs (250–300 g) were employed. Briefly, a 50 cm portion of ileum proximal to the caecum was removed, after discarding the terminal 20 cm. Ileal segments (3 cm) were cleaned by passing Krebs-Henseleit buffer containing 3 μM mepyramine gently through the ileum using a Pasteur pipette (size: 13.8 cm length, 0.65 cm diameter). To avoid unnecessary damage to the tissue, Krebs-Henseleit buffer was passed through the ileal segment, while it was lying horizontally on a petri dish. Therefore, the ileum was not over-distended and the buffer flowed through with ease. Each segment was then passed over a Pasteur pipette and the longitudinal muscle layer and adhering myenteric plexus was teased away using moist cotton wool, by stroking tangentially away from the mesenteric attachment. The tissues were suspended in 20 ml organ baths containing Krebs-Henseleit buffer at 37±1° C. and gassed with 95% $CO_2$/5% $O_2$. The tissues were ligated to two parallel stainless steel wires, situated between two platinum electrodes (0.76 cm length, 0.06 cm diameter). All measurements were recorded isometrically (Grass FTO3 transducer). Following an initial loading tension of 1 g, the tissues were stimulated with electrical pulses at a frequency of 0.1 lHz and a pulse duration of 0.5 msec, as described by Kosterlitz & Watt (Br. J. Pharmacol. 1968, 266–276). Initially, the tissues were stimulated at supramaximal (1.3 fold times maximal) voltage for a period of 30 min and then the tissues were washed and re-stimulated. A "sighter dose" of the selective histamine $H_3$-receptor agonist, R-(α)-methylhistamine (0.3 μM) (Arrang el al. Nature, 1987, 117–123), was administered. Upon generation of response, the "sighter dose" was removed from the tissues by "washout" (6 washes over 60 min) and during this period the electrical stimulation was switched off. The tissues were then re-stimulated and allowed to stabilise prior to the addition of drug treatments, which were allocated on a randomised block basis to the organ baths. Following the incubation period, a single cumulative E/[A] curve was obtained. The experimental E/[A] curve data was expressed as the percentage inhibition of the peak height of electrically-stimulated contraction. Antagonist affinity values were calculated from the degree of rightward shift of the R-(α)-methylhistamine E/[A] curves using Schild's methods (Arunlakshana & Schild Br. J. Pharmacol, 1959, 48–58). The results are set out in Table 1. Typical variance in this assay is ±0.15 log units.

TABLE 1

| Example No. | $pK_B$ (functional assay) – ileum |
| --- | --- |
| 1 | 6.91 |
| 2 | 6.62 |
| 3 | 6.45 |
| 4 | 5.75 |
| 5 | <5.0 |
| 6 | 6.05 |
| 7 | 7.35 |
| 8 | 5.62 |

Histamine $H_3$ radioligand binding assay—guinea pig ileum

Preparation of Membranes

Male Dunkin Hartley guinea pigs (200–300 g) were used. The small intestine was rapidly removed (cut ⁻5 cm from caecum and 5 cm from stomach) and placed in ice-cold 20 mM Hepes-NaOH buffer (pH7.4 at 21±3° C.). The tissue was cut into ⁻10 cm segments, flushed through with ice-cold 20 mM Hepes-NaOH buffer and placed in a beaker containing fresh buffer at 4° C. 10 cm segments of ileum were threaded onto a glass pipette and the longitudinal muscle myenteric plexus was peeled away from the circular muscle using damp cotton-wool. Longitudinal muscle myenteric plexus was immediately placed in ice-cold Viaspan® solution (⁻100 ml for tissue from 3 guinea pigs) and placed in the refrigerator for 24 hours.

Pre-soaked tissue was weighed and minced with scissors. The tissue was then homogenised in Viaspan® using a polytron (Kinematica AG; PT-DA 3020/2TS, 3×⁻1–2s). 50 ml of 500 mM Tris HCl (pH6.9 at 21±3° C.) was added to the tissue and the mixture centrifuged at 39,800×g for 12 min at 4° C. The supernatant was discarded and rehomogenised in 100 ml ice-cold 20 mM Hepes-NaOH buffer (pH7.4 at 21±3° C.) using a teflon-in-glass homogeniser (setting 10; 3×). The homogenate was recentrifuged at 39,800×g and the pellet resuspended in 20 mM Hepes-NaOH buffer (pH7.4 at 21±3° C.), to a tissue concentration of 50 mg.ml$^{-1}$, using a polytron (Brinkman, PT10, 3×$^{-1}$s).

Incubation Conditions

Guinea pig ileum longitudinal muscle myenteric plexus membranes (400 μl) were incubated for 165 min at 21±3° C. in a final volume of 500 μl with 20 mM Hepes-NaOH buffer containing [$^3$H]-R-α-methylhistamine (50 μl; 3 nM) and competing compound. Total and non-specific binding of [$^3$H]-R-α-methylhistamine were defined using 50 μl of buffer and 50 μl of 10 μM thioperamide, respectively. The assay was terminated by rapid filtration through Whatman GF/B filters, presoaked (2 hr) in 0.1% polyethyleneimine, using a Brandell Cell Harvester. The filters were washed (3×3 ml) with ice-cold 50 mM Tris-HCl (pH6.9 at 21±3° C.), transferred into scintillation vials, 5 ml liquid scintillation cocktail was added and after 4 hours the bound radioactivity was determined by counting (4 min) in a Beckman liquid scintillation counter.

Data Analysis

Data are analysed using GraphPad prism and the general equation for a competition curve with variable Hill slope ($n_H$).

$$Y = \text{Non-specific binding} + \frac{(\text{Total binding} - \text{Non-specific binding})}{1 + 10^{((\log IC_{50} - X) \cdot n_H)}}$$

where

X is the log concentration of competing compound,
Y is the binding obtained at each concentration of X,
pIC$_{50}$ is the concentration of the competitor required to compete for half of the specific binding.
The IC$_{50}$ is converted to the K$_I$ using the Cheng Prusoff equation, $$K_I = IC_{50}(1 + (L/K_D))$$

where

IC$_{50}$ is the concentration of competitor required to compete for half the specific binding,
L is the radioligand concentration used,
K$_D$ is the equilibrium dissociation constant for the radioligand determined by saturation experiments.
The results are set out in Table 2. Typical variance in this assay is ±0.12 log units.

TABLE 2

| Example No. | pK$_I$ (binding assay) – ileum |
|---|---|
| 1 | 7.37 |
| 3 | 7.87 |
| 5 | 5.53 |
| 6 | 5.78 |

Histamine H$_3$ radioligand binding assay—guinea pig cortex

Preparation of Membranes

Male Dunkin Hartley guinea pigs (200–300 g) were used. The whole brain was removed and immediately placed in ice-cold 20 mM Hepes-NaOH buffer (pH7.4 at 21±3° C.). The cortex was dissected, weighed and homogenised in ice-cold 20 mM Hepes-NaOH buffer (pH7.4 at 21±3° C.) (50 ml/guinea-pig cortex) using a polytron (Kinematica AG; PT-DA 3020/2TS, 3×3s). The homogenate was centrifuged at 100×g for 5 min and the supernatants pooled and stored at 4° C. The pellets were rehomogenised in fresh ice-cold buffer (80 ml) and recentrifuged (100×g for 5 min). The supernatants were pooled and pellets rehomogenised and recentrifuged (100×g for 5 min). All supernatants were pooled and centrifuged at 39,800×g for 12 min at 4° C. The final pellet was resuspended in 20 mM Hepes-NaOH buffer (pH7.4 at 21±3° C.) to a tissue concentration of 7.5 mg.ml$^{-1}$, using a teflon-in-glass homogeniser.

Incubation Conditions and Data Analysis

These were essentially identical to those used for the guinea pig ileum myenteric plexus assay described above, except that the final assay concentration of [$^3$H]-R-α-methylhistamine was 0.1 nM. The results are set out in Table 3. Typical variance in this assay is ±0.12 log units.

TABLE 3

| Example No. | pK$_I$ (binding assay) – cortex |
|---|---|
| 1 | 7.33 |
| 2 | 5.38 |
| 3 | 8.59 |
| 4 | 6.94 |
| 5 | 5.20 |
| 6 | 7.36 |
| 7 | 9.29 |
| 8 | 6.30 |

What is claimed is:

1. A compound of the formula

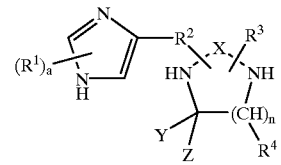

I wherein R$^1$ is selected from C$_1$ to C$_6$ alkyl, C$_1$ to C$_6$ alkoxy, C$_1$ to C$_6$ alkylthio, carboxy, carboxy (C$_1$ to C$_6$) alkyl, formyl, C$_1$ to C$_6$ alklcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulfamoyl and cyano;

the moiety

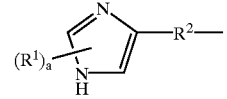

replaces any available hydrogen atom on a carbon or nitrogen atom in the ring which includes X;

R$^2$ is C$_1$ to C$_8$ hydrocarbylene in which one or more hydrogen atoms may be replaced by halogen atoms, and up to 2 carbon atoms may be replaced by oxygen, nitrogen or sulfur atoms, provided that R$^2$ does not contain a —O—O— group;

R$^3$ replaces any available hydrogen atom on a carbon or nitrogen atom in the ring which includes X, and is hydrogen or $C_1$ to $C_{15}$ hydrocarbyl, in which one or more hydrogen atoms may be replaced by halogen atoms, and up to 3 carbon atoms may be replaced by oxygen, nitrogen or sulfur atoms, provided that $R^3$ does not contain a —O—O— group;

the (or each) $R^4$ group is independently selected from H, non-aromatic $C_1$ to $C_6$ hydrocarbyl, and aryl ($C_1$ to $C_3$ alkyl);

X is —SO— or —$SO_2$—

Y and Z are each hydrogen, or together represent =O or =N—$R^5$, wherein $R^5$ is H, non-aromatic $C_1$ to $C_6$ hydrocarbyl, or aryl ($C_1$ to $C_3$ alkyl), or one of Y and Z is non-aromatic $C_1$ to $C_6$ hydrocarbyl, or aryl ($C_1$ to $C_3$ alkyl), and the other is H;

a is from 0 to 2; and n is 1 or 2 or a pharmaceutically acceptable salt thereof.

2. A compound according to claim 1 wherein a=0.

3. A compound according to claim 1 wherein n=1.

4. A compound according to claim 1 wherein $R^3$ is hydrogen, cycloalkyl ($C_1$ to $C_3$) alkyl or aryl($C_1$ to $C_3$)alkyl.

5. A compound according to claim 1 wherein $^2$ is $C_1$ to $C_3$ hydrocarbylene.

6. A compound according to claim 1 wherein $R^3$ and the moiety

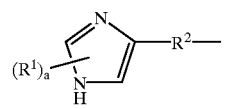

are each attached to a nitrogen atom in the ring which includes X.

7. A pharmaceutical composition comprising a therapeutically effective amount of a compound according to claim 1, and a physiologically acceptable diluent or carrier.

8. A method of treating hypersensitive bodily reactions in a patient, comprising administering to said patient an effective amount of a compound according to claim 1.

9. The method of claim 8, wherein said hypersensitive reaction is an allergic rash, hayfever or asthma.

10. A method of treating disorders associated with excessive levels of histamine in a patient, comprising administering to said patient an effective anti-histamine amount of a compound according to claim 1.

11. The method of claim 10, wherein said disorder is selected from the group consisting of an allergic rash, hayfever, asthma, sleeplessness, convulsion, depression, poor cerebral circulation and irritable bowel syndrome.

12. A prodrug, wherein in vivo degradation of said prodrug yields a compound of claim 1.

* * * * *